(12) United States Patent
Finger

(10) Patent No.: US 7,553,486 B2
(45) Date of Patent: Jun. 30, 2009

(54) ANTI-VEGF TREATMENT FOR RADIATION-INDUCED VASCULOPATHY

(76) Inventor: Paul Theodore Finger, 115 E 61$^{st}$ St., New York, NY (US) 10021

( * ) Notice: Subject to any disclaimer, the term of this patent is extended or adjusted under 35 U.S.C. 154(b) by 0 days.

(21) Appl. No.: 11/598,302

(22) Filed: Nov. 13, 2006

(65) Prior Publication Data

US 2008/0112952 A1   May 15, 2008

(51) Int. Cl.
*A61K 39/395* (2006.01)
*A61K 51/10* (2006.01)
*C12P 21/08* (2006.01)
*C07K 16/22* (2006.01)
*A61F 9/01* (2006.01)
*A61N 5/10* (2006.01)

(52) U.S. Cl. ............... 424/130.1; 424/133.1; 424/141.1; 424/142.1; 424/427; 424/1.11; 430/387.1; 430/387.3; 430/388.1; 430/388.15; 430/388.23; 600/3

(58) Field of Classification Search .............. None
See application file for complete search history.

(56) References Cited

U.S. PATENT DOCUMENTS 6,378,526 B1 * 4/2002 Bowman et al. ............ 128/898
6,524,581 B1 * 2/2003 Adamis .................... 424/130.1

OTHER PUBLICATIONS

Gunduz et al, Archives of Ophthalmology 117(5): 609-614, 1999.*
Lessell et al, J Neuro-Ophthalmol 24(3): 243-250, 2004.*
Ahmadieh et al, Int Ophthalmol 26: 191-193, 2005.*
Avery et al, Ophthalmology 113: 1695-1705, Oct. 2006.*
Lommatzsch et al, Graefe's Arch Clin Exp Ophthalmol 232: 482-487, 1994.*
Witte et al, Cancer Metastasis Reviews 17: 155-161, 1998.*
Rosenfeld et al, Ophthalmology 112: 1048-1053, 2005.*
Hass et al, Ophthalmology 109: 909-913, 2002.*
Stryer et al, in Biochemistry, Third edition, W H Freeman Company, New York, pp. 31-33, 1998.*
Ngo et al., The Protein Folding Problem and Tertiary Structure Prediction, pp. 492-495, 1994.*

* cited by examiner

*Primary Examiner*—Phuong Huynh
(74) *Attorney, Agent, or Firm*—William B. Gowanlock

(57) ABSTRACT

An anti-VEGF method for treating undesirable conditions resulting from radiation-induced vasculopathy. In a specific application, the method is applied to these undesirable conditions found in an eye.

17 Claims, 1 Drawing Sheet

FIG. 1

TABLE 1 — PATIENT, TUMOR AND RADIATION CHARACTERISTICS

| Patient | Age | Sex | Eye | Tumor Location* | Size* Length | Size* Width | Size* Height | Plaque Size | Distance to Fovea** | Distance to Optic Nerve** | Dose (Gy)*** Fovea |
|---|---|---|---|---|---|---|---|---|---|---|---|
| 1 | 56 | Female | OD | 10:30PE | 10.0 | 10.0 | 4.0 | 14.0 | 2.0 | 4.0 | 80.3 |
| 2 | 34 | Male | OS | 11:30P | 10.0 | 9.0 | 3.6 | 14.0 | 2.0 | 0.0 | 49.0 |
| 3 | 59 | Female | OS | 5:00PE | 10.9 | 9.1 | 2.5 | 16.0 | 0.0 | 2.0 | 148.1 |
| 4 | 50 | Female | OD | 9:00PE | 10.0 | 9.0 | 3.4 | 14.0 | 4.0 | 7.5 | 47.7 |
| 5 | 71 | Female | OD | 12:00P | 9.6 | 9.7 | 2.9 | 14.0 | 2.0 | 3.0 | 68.9 |
| 6 | 71 | Female | OS | 11:00P | 11.5 | 13.0 | 3.0 | 18.0 | 4.0 | 0.0 | 41.4 |
| Mean | 56.8 | | | | 10.3 | 10.0 | 3.2 | 15.0 | 2.3 | 2.8 | 72.6 |

* P = Posterior, E = Equator
** in mm
*** Gray units for absorbed dose of radiation

FIG. 2

TABLE 2 — RESULTS DUE TO TREATMENT WITH ANTI-VEGF

| Patient | Visual Acuity Pre | Visual Acuity Post | Visual Disturbance | Macular Edema | Retinal Hemorrhage | Retinal Exudate | Cotton Wool Spots | Retinal Microaneurysms | Anti-VEGF Injections | Total Dosage* | Follow-up** |
|---|---|---|---|---|---|---|---|---|---|---|---|
| 1 | 25 | 25 | Improved | Regression | Regression | Regression | Regression | Stable | 3 | 3.75 | 5 |
| 2 | 320 | 100 | Improved | Regression | Regression | None | None | Regression | 3 | 3.75 | 3 |
| 3 | 20 | 20 | Improved | Regression | Regression | None | Regression | Regression | 3 | 3.75 | 5 |
| 4 | 20 | 20 | No Change | Regression | Stable | None | None | Stable | 1 | 1.25 | 2 |
| 5 | 80 | 80 | Improved | Regression | Regression | Regression | Regression | Regression | 3 | 3.75 | 8 |
| 6 | 32 | 20 | Improved | Regression | Regression | Regression | Regression | Regression | 4 | 5.00 | 5 |
| | | | | | | | | Mean | 2.8 | 3.54 | 4.7 |

* in mg
** in months

ANTI-VEGF TREATMENT FOR RADIATION-INDUCED VASCULOPATHY

FIELD OF THE INVENTION

The present invention relates to treatment for an organ for damage resulting from exposure of the organ to radiation. More specifically, it is a method for stabilizing or regressing damage (i.e., a condition that is undesirable) to an organ, due to radiation exposure of the organ occurring as part of a radiation treatment, to improve, or avoid loss of additional, organ function.

BACKGROUND

Radiation therapy involves the use of high-energy waves or streams, commonly referred to as radiation, that induce ionization in tissue for the treatment of disease. Radiation therapy may be referred to by such terms a radiotherapy, x-ray therapy, gamma-ray therapy, beta-ray therapy, charged-particle therapy, or irradiation.

One disease commonly treated using radiation therapy is cancer. Cancer is a cellular disease where abnormal cells, commonly referred to as cancer cells, grow and divide more rapidly than the normal cells around them. In radiation therapy, therapy equipment aims specific amounts of radiation at these cells, e.g., tumors or areas of the body. Radiation in therapeutic doses kills cancer and intrinsic vascular cells, thus preventing them from growing and dividing.

Radiation administered during radiation therapy not only acts on the cancer cells, but it also acts on proximate normal cells. To limit the effect of radiation on normal cells, doctors carefully limit the doses of radiation and spread the treatments out over time. Additionally, shielding of normal cells is also used. Even with these precautions, an organ having cancer cells therein wherein the cancer cells are being treated by radiation may have proximate normal cells in the organ damaged. Additionally, normal cells in other organs may be damaged. For example, treatment of a nasal cancer might adversely affect normal cells in an eye.

In a number of cases, normal cells damaged during radiation therapy will recover, but in some cases, they will not. One complication of radiation treatment is radiation-induced vasculopathy. Some radiation therapies that may cause radiation-induced vasculopathy include plaque brachytherapy, external beam irradiation, or proton beam.

In ophthalmic plaque brachytherapy, a plaque, which is a small generally metallic object containing radioisotopes (e.g., radioactive seeds), is surgically implanted on the exterior of the eye. The plaque is typically sutured to the outside wall of the eye (i.e., the sclera) proximate an intraocular melanoma (a type of cancer) located therein. The radioisotope associated with the plaque emits radiation that penetrates the sclera and treats the melanoma. Generally, the plaque provides shielding so that proximate organs, and thus the normal cells therein, are protected from the radiation, at least to some degree. The plaque generally remains on the eye until the intraocular melanoma has received a therapeutic dose of radiation (e.g., enough to destroy it). The plaque is then surgically removed.

Intraocular melanomas are classified into three general categories based on size. In accordance with the American Joint Committee on Cancer (AJCC) and COMS Staging Criteria, intraocular melanomas up to 2.4 millimeters in height and less than 10 mm in width are classified as T1 or small. Intraocular melanomas that are more than 2.4 to 9.9 millimeters in height and less than 16 mm in width are considered T2 or medium. Those intraocular melanomas that are 10 mm or larger in height and/or 16 mm or larger in width are T3 or COMS-large.

As the size of the intraorgan cancers, such as intraocular melanomas, increases, the amount of radiation required to treat them effectively also increases. Unfortunately, as the radiation level is increased, the probability of irreversible damage to otherwise normal cells increases. More specifically, the incidental damage to normal cells may not be reversible, in whole or in part, or the damage may cause other problems. Thus, in some cases, the organ might be saved, but the functionality of that organ may be severely affected. In other cases, the effect could lead to a loss of the function of the organ (e.g., in the case of an eye, blindness).

Two types of radiation-induced vasculopathy occurring in the eye from radiation therapy, on either the eye or an adjacent organ, are retinopathy and neuropathy. These two conditions are common sight-limiting complications of ophthalmic radiation therapy. Radiation retinopathy is associated with the eye's retina. Where it involves the macula (i.e., radiation maculopathy), blindness is a significant risk. Radiation neuropathy is generally associated with the eye's optic nerve, and for patients with this condition blindness is also a significant risk.

The risk of radiation-induced vasculopathy is a function of the effective dose of radiation required to treat the cancer, the pre-existing presence of systemic disease such as diabetes, and the use of radiation sensitizers (i.e., pre-treatments such as chemotherapy designed to increase the effectiveness of the radiation therapy).

Radiation retinopathy, which may present with the symptoms of loss of visual acuity or visual disturbance, includes such damage as obliterative endarteritis (endothelial cell loss and thickened vessel walls) and intraretinal microangiopathy. This damage (or side effect) presents as tissue ischemia caused by undesirable conditions such as vascular occlusions, capillary dropout and leakage (hemorrhages, exudation and edema) and microaneurysms. If any of these undesirable conditions is left untreated, the undesirable condition may worsen and/or cause other undesirable conditions, such as neovascularization, that ultimately lead to a loss of visual acuity and/or visual disturbance. While some of these undesirable conditions are controllable using laser photocoagulation, not all are. In particular, where these undesirable conditions occur because of treatment of subfoveal and macular choroidal melanomas in the eye, they are not amenable to or controllable by laser techniques.

Radiation-induced optic neuropathy (RON), while uncommon, often results in blindness. Posterior RON occurs on the posterior of the eye, thus its pathophysiologic events are hidden. Posterior RON is typically associated with external beam irradiation. Anterior RON occurs on the anterior of the eye (i.e., visible by looking through the eye's lens). Anterior RON is typically associated with ophthalmic plaque or proton beam irradiation.

Posterior RON typically presents with the symptom of loss of visual acuity, while anterior RON typically presents with the symptom of visual disturbance, such as "central haze." In patients with anterior RON, ophthalmic examination reveals optic disc microangiopathy, edema, hemorrhage, neovascularization. Additionally, radiation retinopathy may also be present.

RON is also classified as early or late. In the case of early RON, it occurs within several weeks of irradiation and is characterized by acute inflammation leading to optic nerve pallor. Late RON occurs years after treatment and is characterized by vasculitis, necrosis, and optic disc pallor, all of which are generally irreversible.

What is needed in the art is a treatment for radiation-induced vasculopathy to stabilize, or regress, the undesirable conditions of radiation therapy on organs, so that larger cancers, where these undesirable conditions pose a more significant risk as to overall organ function, can be treated effectively such that a functioning organ, at least to some degree, is preserved.

SUMMARY OF THE INVENTION

This invention is a method for treating the undesirable conditions resulting from radiation therapy on an organ. More specifically, it is a method for treating undesirable conditions resulting from radiation-induced vasculopathy. In a specific application, the method is applied to the undesirable conditions found in an eye.

In the method, a therapeutic dose of an anti-VEGF (vascular endothelial growth factor), presently sold as bevacizumab (AVASTIN®), ranibizumab (LUCENTIS®), and pegaptanib sodium (MACUGEN®), is administered intraorgan or intravenously. Present anti-VEGF medications are a humanized monoclonal antibody to vascular endothelial growth factor (VEGF). In the case of eye, intraorgan administration is more specifically referred to as intravitreally.

A therapeutic dose is defined as the total dose, whether applied in a single application, or in a number of partial doses administered in a regimen of applications spread over time (i.e., having an interval therebetween) wherein the sum of partial doses is the total dose. In the case where partial doses are administered, each partial dose need not be the same, nor does the interval therebetween need to be the same. A therapeutic dose stabilizes, or regresses, at least one undesirable condition associated with the harmful effects of radiation-induced vasculopathy in at least some patients.

These and other features, aspects, and advantages of embodiments of the present invention will become apparent with reference to the following description. It is to be understood, however, that the drawings are designed solely for the purposes of illustration and not as a definition of the limits of the invention.

BRIEF DESCRIPTION OF THE DRAWINGS

FIG. 1 is a table titled "Patient, Tumor and Radiation Characteristics."

FIG. 2 is a table titled "Results due to Treatment with Anti-VEGF."

DETAILED DESCRIPTION

The present invention is a method of treating radiation-induced vasculopathy resulting from radiation therapy of an organ. Histopathology of radiation-induced vasculopathy reveals in both the destruction of the vascular endothelial cells, and pericytes. Radiation vasculopathy includes such damage as obliterative endarteritis (endothelial cell loss and thickened vessel walls) and intraretinal microangiopathy. This damage presents as tissue ischemia caused by undesirable conditions such as vascular occlusions, capillary dropout and leakage (hemorrhages, exudation and edema) and microaneurysms. If any of these undesirable conditions is left untreated, the undesirable condition may worsen and/or cause other undesirable conditions, such as neovascularization, that ultimately lead to a loss of organ function (e.g., where the organ is an eye, the loss of organ function presents as the symptoms of loss of visual acuity and/or visual disturbance).

The method of the present invention involves treating these undesirable conditions of radiation-induced vasculopathy in a patient by administering intra-organ a therapeutic dose of an anti-VEGF (vascular endothelial growth factor), presently sold as bevacizumab (AVASTIN®), ranibizumab (LUCENTIS®), and pegaptanib sodium (MACUGEN®).

A therapeutic dose is defined as the total dose, whether applied in a single application, or in a number of partial doses administered in a regimen of applications spread over time (i.e., having an interval therebetween) wherein the sum of partial doses is the total dose. In the case where partial doses are administered, each partial dose need not be the same, nor does the interval therebetween need to be the same. A therapeutic dose stabilizes, or regresses, at least one undesirable condition associated with the harmful effects of radiation-induced vasculopathy in at least some patients.

A dose may be administered intra-organ or intravenously. Where the therapeutic dose is given in a single dose, it will be administered intra-organ or intravenously. Where the therapeutic dose is comprised of a series of partial doses, a particular partial dose may be administered either intra-organ or intravenously. Therefore, for a regimen, the administration may be all intra-organ, all intravenously, or some combination wherein at least some of the therapeutic dose is administered intra-organ.

While "patient" typically refers to a human, those of skill in the art will appreciate that the methods of the invention can be used to treat these undesirable conditions in any mammal, including non-human primates. As used herein, "treating" refers to taking the steps to obtain beneficial or desired results to stabilize, improve, or regress the undesirable condition, as the case may be. It should also be appreciated, that, as there are variations among patients, the effects of the method thereon may offer benefit to some but not all. In addition, the precise benefit among patients may vary.

In accordance with the present invention, the method was used to treat radiation vasculopathy (e.g., radiation retinopathy and radiation neuropathy) resulting from ophthalmic plaque brachytherapy of subfoveal or macular choroidal melanomas, which were not amenable to, or uncontrolled by, laser photocoagulation. Ophthalmic plaque brachytherapy uses a plaque having a radiation source associated therewith to irradiate a tumor to induce a progressive closure of the tumor, e.g., melanoma, and retinal vessels within the plaque's target zone, which is beneath the plaque. In the treatment, the patients received varying amounts of radiation, based upon the size of their melanomas. Radiation doses ranged from about 41 Gy to 148 Gy. No complications from the surgery to implant and remove the plaque were encountered.

Clinically, the undesirable conditions of radiation retinopathy present with the symptoms of loss of visual acuity and/or visual disturbance. Examination reveals one or more of the following undesirable conditions—microaneurysms, vascular occlusions, capillary dropout and leakage, such as hemorrhage, exudation and edema. If left untreated, these undesirable conditions foreshadow the potential for additional acuity impairment and visual disturbance, and potentially blindness. In other words, the functioning of the organ will continue to decline potentially to the point of total dysfunction.

In the method, anti-VEGF is injected intravitreally. In one test group, the total dose of anti-VEGF (specifically anti-VEGF bevacizumab sold under the trademark AVASTIN®) ranged from 1.25 mg to 5.00 mg, administered in single doses of 1.25 mg. More specifically, the partial dose rate, or in the case of a single dose the total dose, was 1.25 mg in 0.05 cc. Those skilled in the art of ophthalmic treatment will realize that a single dose of 1.25 mg is considered a practical amount. Studies related to other problems of the eye where intravitreal treatment of anti-VEGF is used, have indicated beneficial single doses ranges of between 0.62 mg and 2.5 mg Thus the single dose for the present invention is considered to be between 0.62 mg and 2.5 mg.

The injections were made into the eye through the pars plana using a 30-gauge needle. As those skilled in the art of ophthalmic treatment will realize, the volume of any injection into the eye must be limited in amount so not as to adversely affect optic nerve perfusion and intraocular pressure. Similar considerations would apply to injections into other organs. Optic nerve perfusion and intraocular pressures were acceptable prior to discharge, and the patients were placed on topical antibiotic therapy for one week. No complications from the injections were encountered. Where the regimen consisted of multiple injections, injections were repeated every six to eight weeks based primarily on changes in visual acuity and macular edema.

More specifically, six patients with radiation retinopathy resulting from plaque brachytherapy for subfoveal or macular choroidal melanomas were treated using the method. See FIG. 1, for individual patient details. Each patient was treated with a plaque having palladium-103 mounted thereon. While individual radiation treatment doses and days of treatment varied, the mean radiation dose was 72.6 Gy given over 7 days.

As shown in FIG. 2, the number of anti-VEGF injections and time, in months, for a follow up varied, with a mean of 2.8 mg and 4.7 months, respectively. Total doses, the sum of all partial doses, or a single total dose, had a mean of 3.4 mg, with a range of 1.25 mg to 5.00 mg. The number of injections varied from 1 to 4, with a mean of 2.8.

Reduction of macular edema was the most consistent and reproducible finding. Where macular edema was reduced, it was typically accompanied by improvements in visual acuity. In addition, there was an overall reduction in the size and distribution of retinal hemorrhages and exudates. In addition, progressions in retinal hemorrhages, exudates or cotton-wool spots (indicative of vascular occlusions and/or capillary dropout) were not noted, thus they were stable.

There was evidence of closure of microaneurysms and intraretinal microangiopathy. The most common finding was decreased vascular permeability, which was evidenced by the sharpening of blood vessel edges when viewed using fluorescein angiography. There was some evidence of reperfusion of previously closed blood vessels.

In the case of patient 1, pretreatment fluorescein photographs revealed the patient suffered hemorrhages, cotton wool spots (indicative of vascular occlusions and capillary dropout), and macular edema (in this case a thickened edematous retina proximate the macula). Optical Coherence Tomography and Scanning Laser Ophthalmoscope imaging (OCT/SLO imaging) revealed a thickened and hyper-reflective nerve fiber layer proximate the macula. More specifically, it was between the optic nerve and the fovea. In addition, it revealed shadowing of the outer retinal layers, and retinal pigment epithelium.

After a regimen of two injections occurring at intervals of 3 to 4 months, OCT/SLO imaging revealed resolution of the macular edema. It further revealed that the macula had returned to its normal contour.

Visual issues (e.g., acuity and disturbance) generally improved. Visual acuity in two cases was improved. Visual disturbance in five cases was improved. In four cases, where visual disturbance resulting from haze and metamorphopsia was reported, improvement was noted. Overall, no patients lost vision due to radiation retinopathy, though vision loss is a common outcome for patients with these types of melanomas and these undesirable conditions.

Side effects appear minimal and transient. Some patients reported seeing "round blue objects" for a day or two after injection. This was attributed to small air bubbles. Bubbles were, however, undetectable using an ophthalmoscope. Optic nerve perfusion and intraocular pressure were also negatively affected, but resolved without anterior chamber paracentesis or pharmacologic intervention. In addition, endophthalmitis, retinal detachment and vitreous hemorrhaging did not occur.

Radiation optic neuropathy, as does radiation retinopathy, presents with the symptoms of loss of visual acuity and/or visual disturbance. These symptoms are caused by the undesirable conditions of microangiopathy, edema, and hemorrhage. The further complication of neovascularization may also be present.

In a case involving radiation-induced optic neuropathy (RON), a 69-year old female patient developed the complication eighteen months after treatment for an AJCC-T2 juxtapapillary choroidal melanoma using ophthalmic plaque brachytherapy. The patient presented with the symptoms of loss of visual acuity (20/32 from 20/20) and visual disturbance (central haze). The ophthalmic plaque brachytherapy used a notched, palladium-103 plaque.

Ophthalmoscopy examination revealed optic disc neovascularization, edema and hemorrhage. Serial OCT/SLO imaging revealed a thickened optic nerve fiber layer, that the optic cup had diminished, and intraretinal fluid surrounded the optic disc. Additionally it revealed neural, perineural and intraretinal edema. The patient was treated initially with an intravitreal injection of anti-VEGF (specifically anti-VEGF bevacizumab sold under the trademark AVASTIN®) at a dose of 1.25 mg in 0.05 cc. Over time, the patient received another five 1.25 mg dose, for a total dose of 6.25 mg.

An examination, using ophthalmoscopy, fundus photography and angiography was performed seven days after treatment. The examination revealed decreased optic disc microangiopathy and hemorrhage, but increased edema. The patient's vision, however, had returned to 20/20 with a subjective resolution of the "central haze."

Six weeks after treatment, the patient was examined again. The examination revealed an improvement in the patient's optic nerve appearance. Serial OCT/SLO imaging revealed that, while the optic disc edema persisted, the optic cup had deepened and the perineural edema diminished. It was decided a second injection, which was at same dose as the first, was prudent.

Six weeks after the second injection (3 months from the initial injection), the patient was again examined. The patient's vision remained stable (20/20) and the optic disc was well perfused and had shaped margins. The neovascularization, however, persisted. Serial OCT/SLO imaging revealed a marked decrease in neural, perineural and intraretinal edema, and optic nerve cup reformation.

A subsequent examination 7 months after the initial injection indicated that the patient was stable.

While there has been illustrated and described what is at present considered to be preferred and alternative embodiments of the claimed invention, it will be appreciated that numerous changes and modifications are likely to occur to those skilled in the art. It is intended in the appended claims to cover all those changes and modifications that fall within the spirit and scope of the claimed invention.

What is claimed is:

1. A method for treating radiation-induced optic neuropathy (RON) comprising the steps of:
   identifying an eye or optic nerve in a patient having at least one undesirable condition of radiation-induced optic neuropathy resulting from radiation treatment applied to the eye or optic nerve; and
   administering intraocullarly a therapeutic dose of a monoclonal antibody or a Fab-binding fragment thereof that binds to VEGF, wherein the therapeutic dose is administered between about 1.25 mg and about 6.25 mg and wherein the therapeutic dose administered stabilizes or regresses the at least one undesirable condition associated with radiation-induced optic neuropathy (RON).

2. The method of claim 1 wherein the monoclonal antibody or the Fab-binding fragment thereof is humanized.

3. The method of claim 2 wherein the monoclonal antibody is bevacizumab.

4. The method of claim 2 wherein the fab-binding fragment is ranibizumab.

5. The method of claim 1 wherein in the step of identifying the eye or optic nerve, the at least one undesirable condition is selected from the group consisting of loss of visual acuity, visual disturbance, leakage, edema, hemorrhage, exudates, cotton wool spots, and microaneurysms.

6. The method of claim 1 wherein the therapeutic dose is administered by more than one injection, each injection defining a partial dose.

7. The method of claim 6 wherein each partial dose is between about 0.62 mg and about 2.5 mg.

8. The method of claim 6 wherein the partial doses have an average of about 1.25 mg.

9. The method of claim 6 wherein each partial dose is approximately equal.

10. The method of claim 6 wherein each injection is separated by an interval of between 6 and 8 weeks.

11. The method of claim 1 wherein the therapeutic dose is administered in one or more injections, and each injection administers 1.25 mg in 0.05 cc.

12. The method of claim 1 wherein in the step of identifying the eye or optic nerve, the identified eye or optic nerve received radiation in an amount between 41 and 148 Gy.

13. A method for treating radiation induced optic neuropathy (RON) of an eye having an intraocular melanoma comprising the steps of:
    examining the eye to determine that an intraocular melanoma is present;
    performing radiation therapy on the eye;
    examining the eye after radiation therapy to determine that at least one undesirable condition associated with radiation-induced optic neuropathy (RON) is present; and
    administering to the eye intraocularly one or more injection of a monoclonal antibody or a Fab-binding fragment thereof that binds to VEGF for at least one symptom associated with radiation-induced optic neuropathy (RON) wherein each injection is 1.25 mg in 0.05 cc.

14. The method of claim 13 wherein the monoclonal antibody or the Fab-binding fragment thereof is humanized.

15. The method of claim 14 wherein the monoclonal antibody is bevacizumab

16. The method of claim 14 wherein the fab-binding fragment is ranibizumab.

17. The method of claim 13 wherein in the step of performing radiation therapy, the radiation therapy includes ophthalmic plaque brachytherapy.

* * * * *